United States Patent
Rago et al.

(10) Patent No.: US 9,820,749 B2
(45) Date of Patent: *Nov. 21, 2017

(54) INTRA-ABDOMINAL PRESSURE TO PROMOTE HEMOSTASIS AND SURVIVAL

(71) Applicant: ARSENAL MEDICAL, INC., Watertown, MA (US)

(72) Inventors: Adam Rago, Falmouth, MA (US); John Marini, Weymouth, MA (US); Gregory T. Zugates, Chemlsford, MA (US); Marc Helmick, Brighton, MA (US); Upma Sharma, Somerville, MA (US)

(73) Assignee: ARSENAL MEDICAL, INC., Watertown, MA (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/597,993

(22) Filed: Jan. 15, 2015

(65) Prior Publication Data

US 2015/0223819 A1 Aug. 13, 2015

Related U.S. Application Data

(63) Continuation-in-part of application No. 14/455,117, filed on Aug. 8, 2014, now Pat. No. 9,522,215, which is a continuation-in-part of application No. 13/209,020, filed on Aug. 12, 2011, now Pat. No. 9,173,817, which is a continuation-in-part of application No. 12/862,362, filed on Aug. 24, 2010, now abandoned.

(51) Int. Cl.
*A61F 2/02* (2006.01)
*A61B 17/12* (2006.01)
*A61L 24/00* (2006.01)
*A61L 24/04* (2006.01)

(52) U.S. Cl.
CPC .......... *A61B 17/12* (2013.01); *A61L 24/0036* (2013.01); *A61L 24/046* (2013.01); *A61B 2017/12004* (2013.01); *A61L 2400/04* (2013.01); *A61M 2210/1021* (2013.01); *A61M 2210/12* (2013.01)

(58) Field of Classification Search
CPC ....... A61F 2/02; A61B 17/12; A61B 2017/12; A61B 2017/12004; A61M 29/00; A61M 29/02; A61L 24/046; A61L 24/0036
See application file for complete search history.

(56) References Cited

U.S. PATENT DOCUMENTS 6,098,010 A * 8/2000 Krener ................. F04D 27/001
105/64.1
6,520,977 B2 2/2003 Piraka
(Continued)

OTHER PUBLICATIONS

Michael Duggan et al: "Self-expanding polyurethane polymer improves survival in a model of noncompressible massive abdominal hemorrhage", Journal of Trauma and Acute Care Surgery, vol. 74, No. 6, Jun. 1, 2013 (Jun. 1, 2003), pp. 1462-1467, XP055351157, US ISSN: 2163-0755, DOI: 10.1097/TA.0b013e31828da937.

*Primary Examiner* — Victor Nguyen

(57) ABSTRACT

Systems, methods and kits for treating hemorrhages within cavities are provided. The methods utilize the application of a rapid spike of pressure to the closed cavity, followed by a steady state pressure or pressures.

13 Claims, 13 Drawing Sheets

(56) References Cited

U.S. PATENT DOCUMENTS

Figure 1:
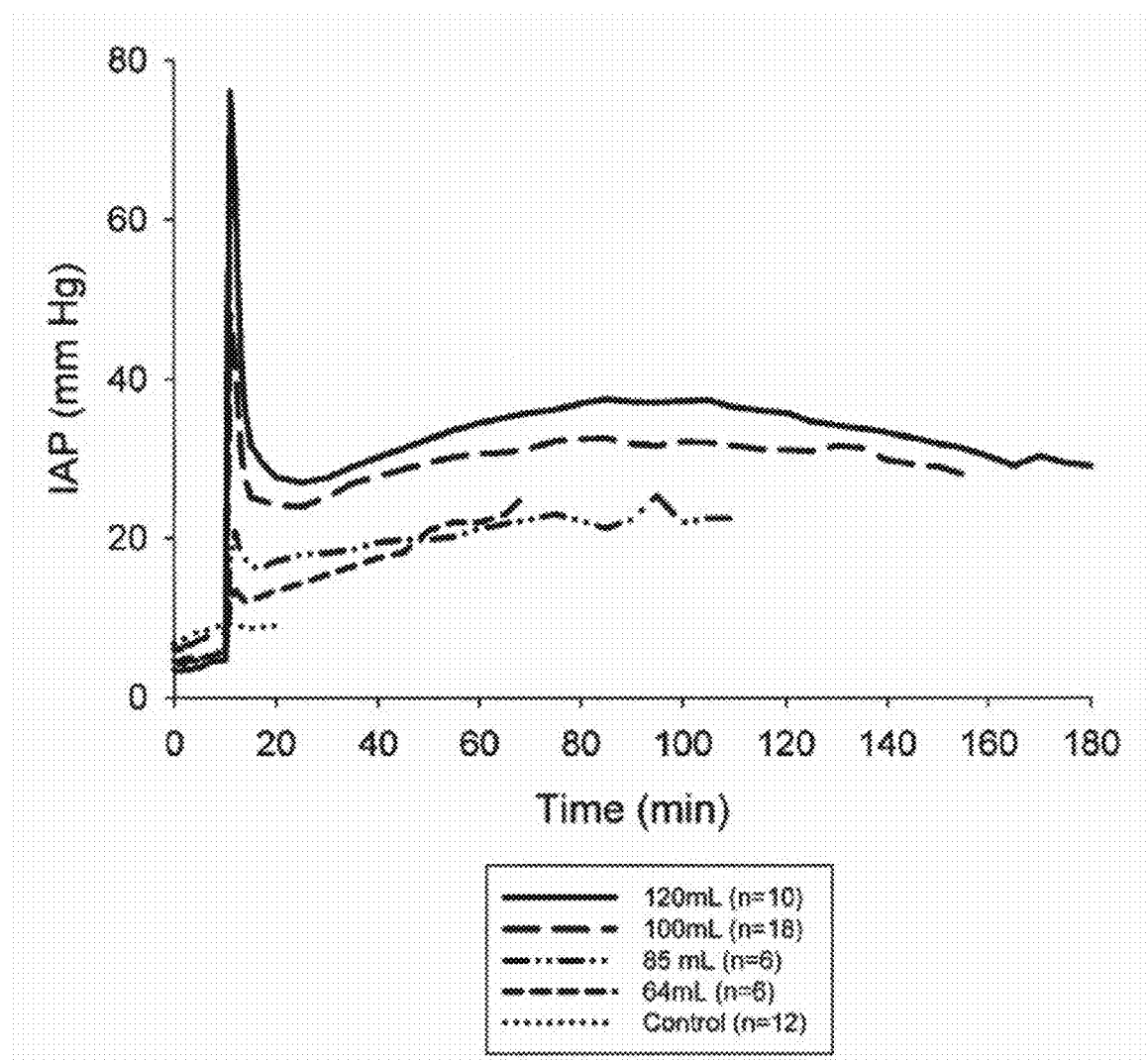

| | | |
|---|---|---|
| 2004/0013715 A1 | 1/2004 | Wnek et al. |
| 2006/0008419 A1* | 1/2006 | Hissink ............... A61L 24/0036 424/45 |
| 2009/0232876 A1 | 9/2009 | Montes et al. |
| 2011/0202016 A1 | 8/2011 | Zugates et al. |
| 2012/0265287 A1 | 10/2012 | Sharma et al. |
| 2012/0308509 A1 | 12/2012 | Mukhopadhyay et al. |
| 2013/0110066 A1 | 5/2013 | Sharma et al. |

\* cited by examiner

INTRA-ABDOMINAL PRESSURE TO PROMOTE HEMOSTASIS AND SURVIVAL

CROSS-REFERENCE TO RELATED APPLICATION

This application is a Continuation-in-Part of U.S. patent application Ser. No. 14/455,117, which claims the benefit of priority to U.S. Provisional Patent Application No. 61/864,368 by Adam Rago et al. entitled "INTRA-ABDOMINAL PRESSURE TO PROMOTE HEMOSTASIS AND SURVIVAL." U.S. patent application Ser. No. 14/455,117 is also a Continuation-In-Part of U.S. patent application Ser. No. 13/209,020 entitled "In Situ Forming Hemostatic Foam Implants," filed Aug. 12, 2011 ("Sharma I") and claiming priority to U.S. patent application Ser. No. 12/862,362 entitled "Systems and Methods Relating to Polymer Foams," filed Aug. 24, 2010 ("Zugates II"), which in turn claims priority to U.S. Provisional Patent Application No. 61/263,314, also entitled "Systems and Methods Relating to Polymer Foams" and filed Jul. 27, 2010 ("Zugates I"). U.S. patent application Ser. No. 14/455,117 makes reference to U.S. Provisional Patent Application No. 61/852,051, filed Mar. 15, 2013 ("Sharma II"). The entire disclosure of each of the foregoing references is hereby incorporated by reference for all purposes.

TECHNICAL FIELD

Systems and methods relating to polymer foams are generally described.

BACKGROUND

In situ forming polymer foams, such as the Arsenal Foam Technology commercialized by Arsenal Medical (Watertown, Mass.), have a number of important biomedical applications including the prevention or treatment of hemorrhage, particularly from noncompressible or difficult-to-visualize wounds, vascular embolization, arteriovenous malformation, AV fistulas, abdominal aortic aneurysm, space filling and bulking (e.g. following surgical resection, or for cosmetic purposes), prevention of tissue adhesion, hernia repair, prevention or treatment of reflux, and temporary or permanent occlusion of body lumens for a variety of applications including sterilization, prevention of calculus migration during lithotripsy, and other applications. The diversity of applications for in situ forming foams reflects significant advantages possessed by such foams relative to existing technology, including, without limitation their incorporation of well characterized, biocompatible materials; the ability to deliver in situ forming foams to closed cavities, for example intravascularly; the ability to deliver in situ forming foams to difficult-to-access body sites; the ability of in situ forming foams to expand into empty space, potential space, or into space filled with blood, support surrounding tissues, and the ability of the foam to fill a body cavity.

Foams are typically generated in situ by delivering and mixing multiple liquid-phase components (such as a polyol component and an isocyanate component, which form a polyurethane foam). Pores within the foam may be formed by a blowing reaction and/or by the entrainment of gas before or during foam formation, and the foam may harden through the formation of cross-links between prepolymers and/or cross-linking agents. When deployed into a body cavity, the liquid components react, driving the expansion and hardening of the foam. The foam applies pressure to the boundaries of the cavity in a dose dependent and time-dependent manner, for example as shown in the pressure curves of FIG. 1. The shapes of these curves are determined by, among other things, the composition and quantity of liquid phase components applied to the body cavity, which govern the rates of the blowing and cross-linking reactions and foam properties (e.g., density or volume expansion, stiffness, pore size, hydrophilicity, absorption capacity).

In situ forming foams are particularly well suited to treating noncompressible hemorrhages in challenging settings, including the battlefield and rural or wilderness settings far from hospital trauma centers. However, in spite of their advantages, in situ forming foams have not been widely used because of the technical challenges associated with developing suitable in situ foaming formulations for different applications and delivering of these formulations to body cavities in quantities sufficient to arrest hemorrhages without causing undesirable side effects of excessive pressure such as compartment syndrome. Additionally, to maximize their efficacy in challenging or remote settings, in situ forming foams should extend patient survival times for a period sufficient to permit evacuation of patients to stations or centers where hemorrhages can be surgically treated.

SUMMARY OF THE INVENTION

Embodiments of the current invention address the challenges described above by providing, in one aspect, a method for treating hemorrhage within a body cavity or potential space that includes applying pressure to an interior boundary of the cavity, including pressure to the injury itself, which pressure is characterized by a transient peak value and by at least one steady state value. In various embodiments, the transient peak value is between 22 mmHg and about 86 mmHg (e.g. 20, 51 and 84 mmHg). The steady state value is, in various embodiments, between about 14 mmHg and about 28 mmHg (e.g. 14 or 28 mmHg). Pressure may be applied, in certain embodiments, by an article placed into the closed cavity, and the article can be a foam which is formed inside of the cavity by applying a formulation that includes one or more liquid phases into the cavity. In some cases, the steady state pressure occurs within three minutes and is followed by the steady state value. The steady state value may be, in some cases, 30%, 50% or 90% of the transient peak value.

In another aspect, the invention relates to a kit for treating hemorrhage in closed cavities that includes (i) a formulation for forming a foam when disposed into a body, which formulation includes at least one liquid phase, and (ii) instructions for performing the method set forth above.

DRAWINGS

In the drawings, like reference characters refer to like features through the different views. The drawings are not necessarily to scale, with emphasis being placed on illustration of the principles of the invention.

FIG. 1 plots intra-abdominal pressure over time for four doses of an in situ forming foam in a severe porcine liver hemorrhage model compared with an untreated control.

Figure 2:
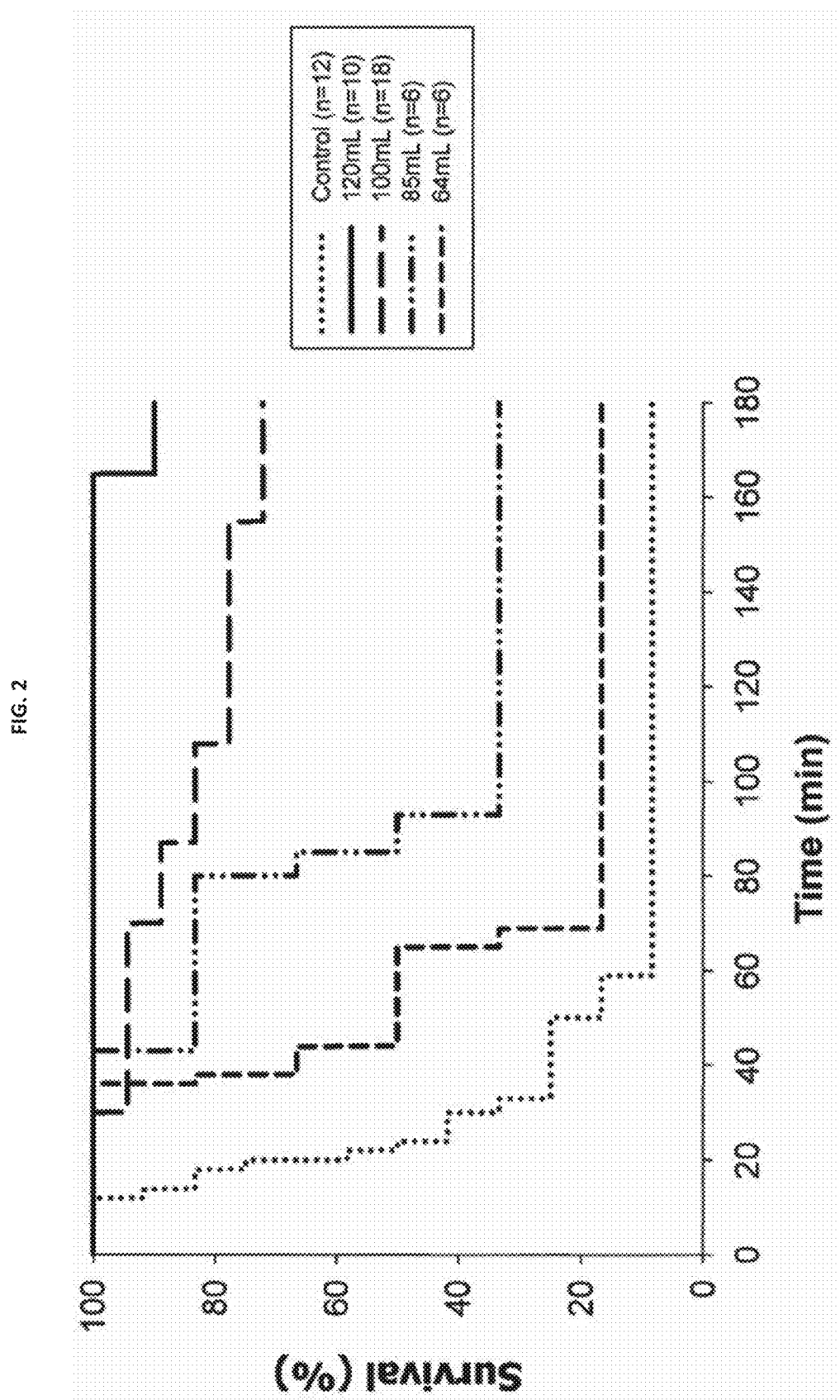

FIG. 2 plots survival curves for porcine treated with four doses of an in situ forming foam in a severe liver hemorrhage model compared with an untreated control.

Figure 3:
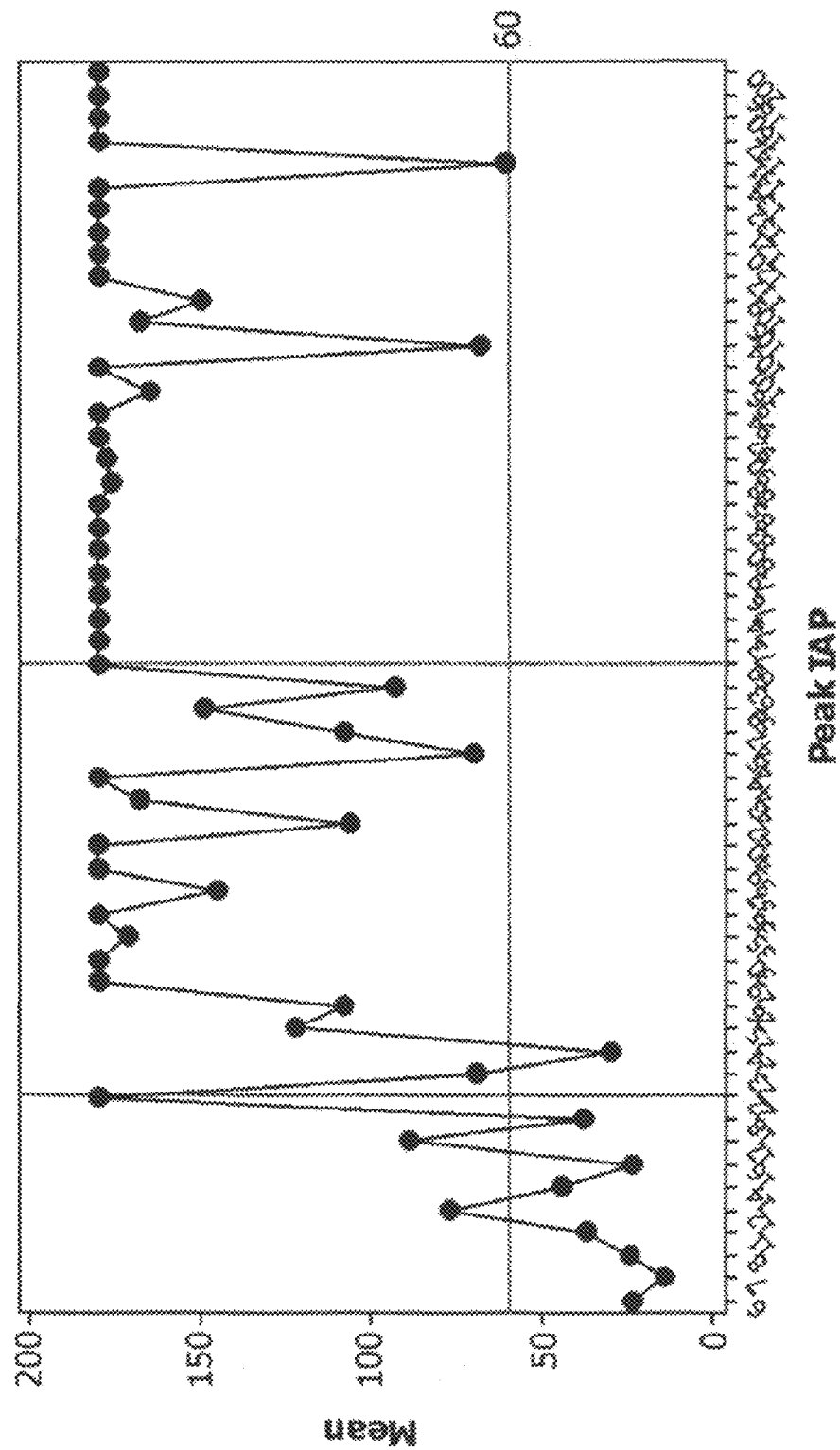

FIG. 3 plots the survival times of 81 animals treated either with in situ forming foams or no foam treatment controls against the peak intra-abdominal pressure measured in each animal in a severe liver hemorrhage model.

Figure 4:
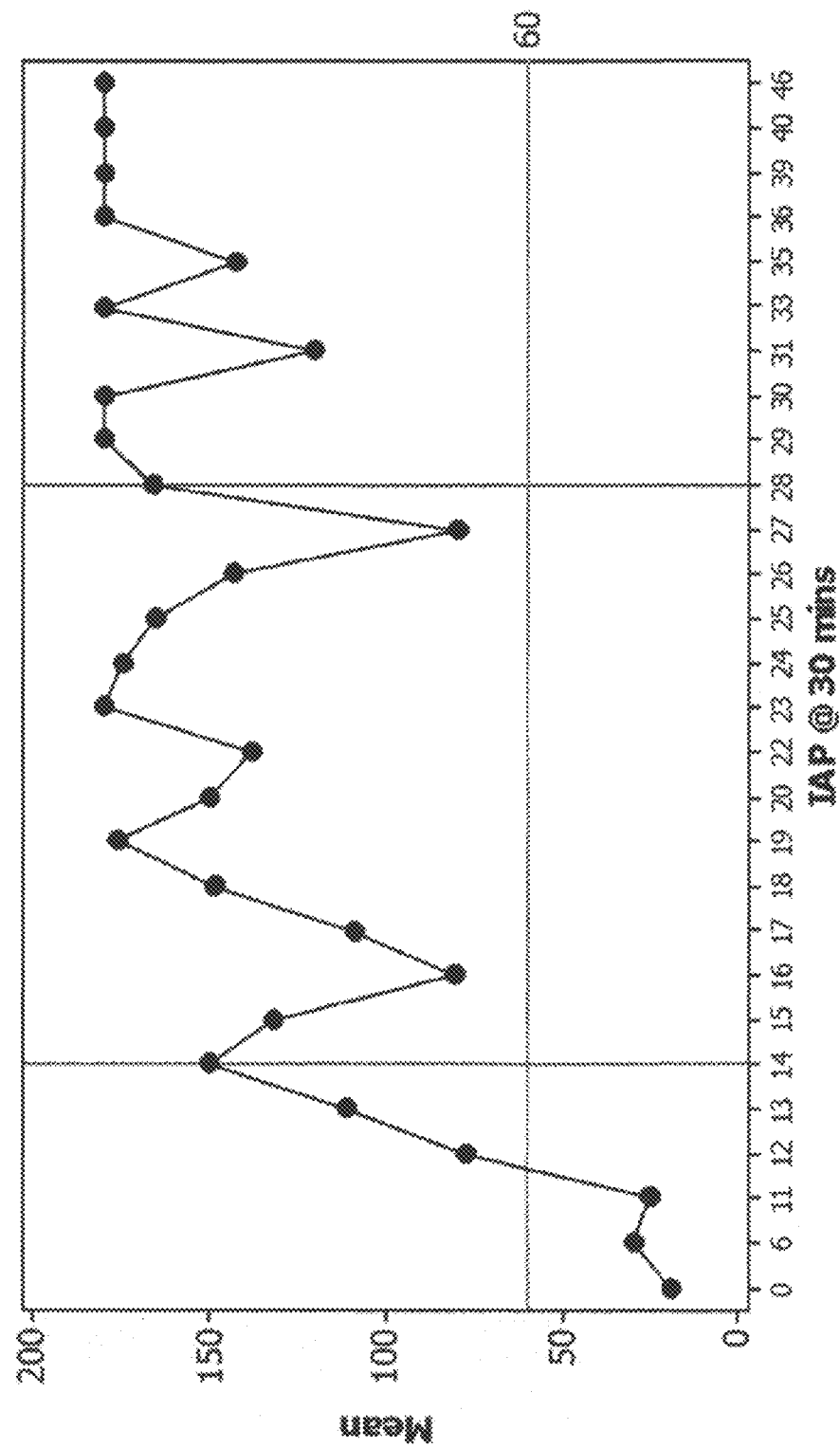

FIG. 4 plots the survival times of 81 animals treated either with in situ forming foams or no foam treatment control animals against the intra-abdominal pressure measured at 30-minutes post injury in each animal in a severe liver hemorrhage model.

Figure 5:
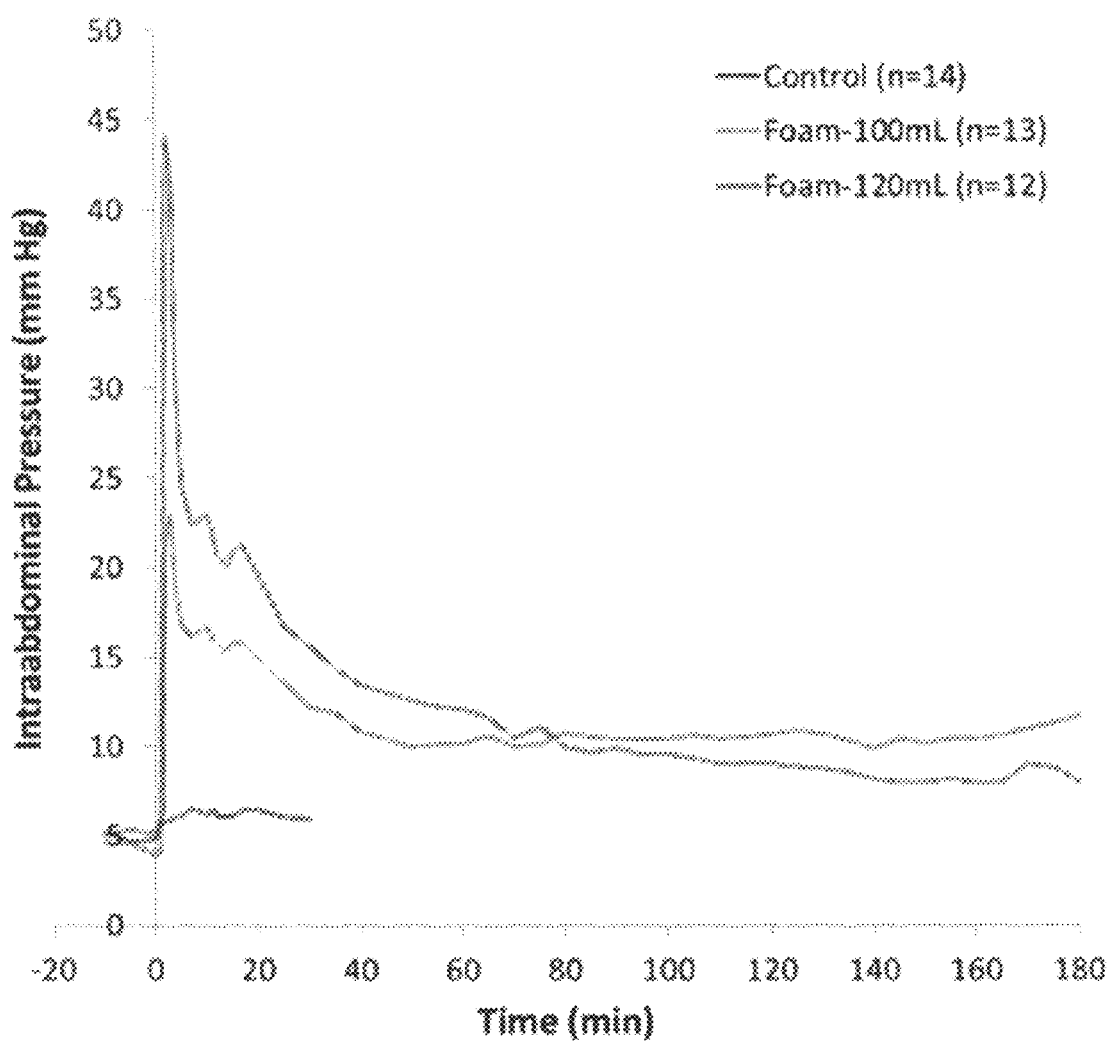

FIG. 5 plots intra-abdominal pressure over time for two doses of an in situ forming foam in a severe arterial hemorrhage model.

Figure 6:
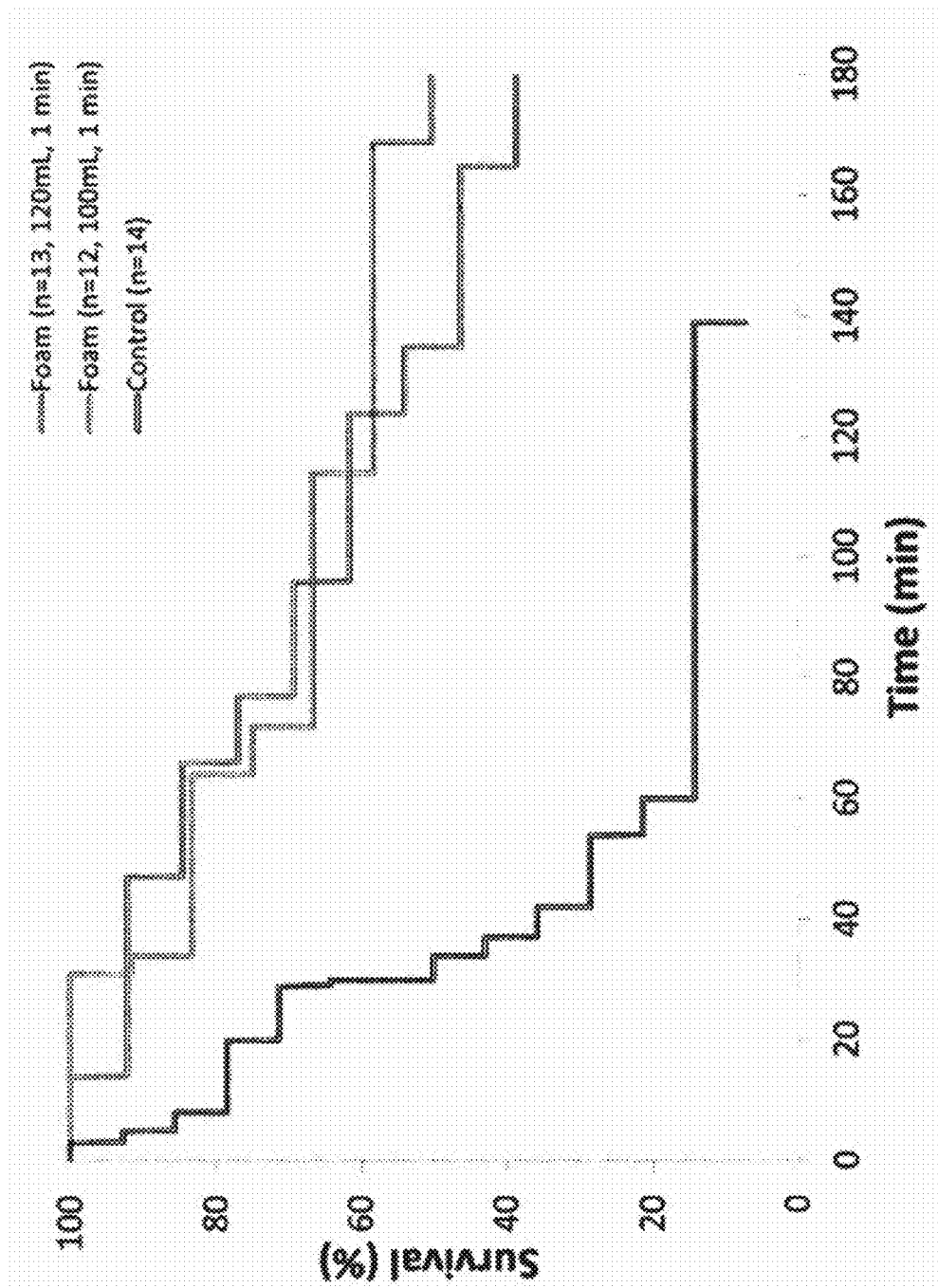

FIG. 6 plots survival curves for animals treated with two doses of an in situ forming foam in a severe arterial hemorrhage model.

Figure 7:
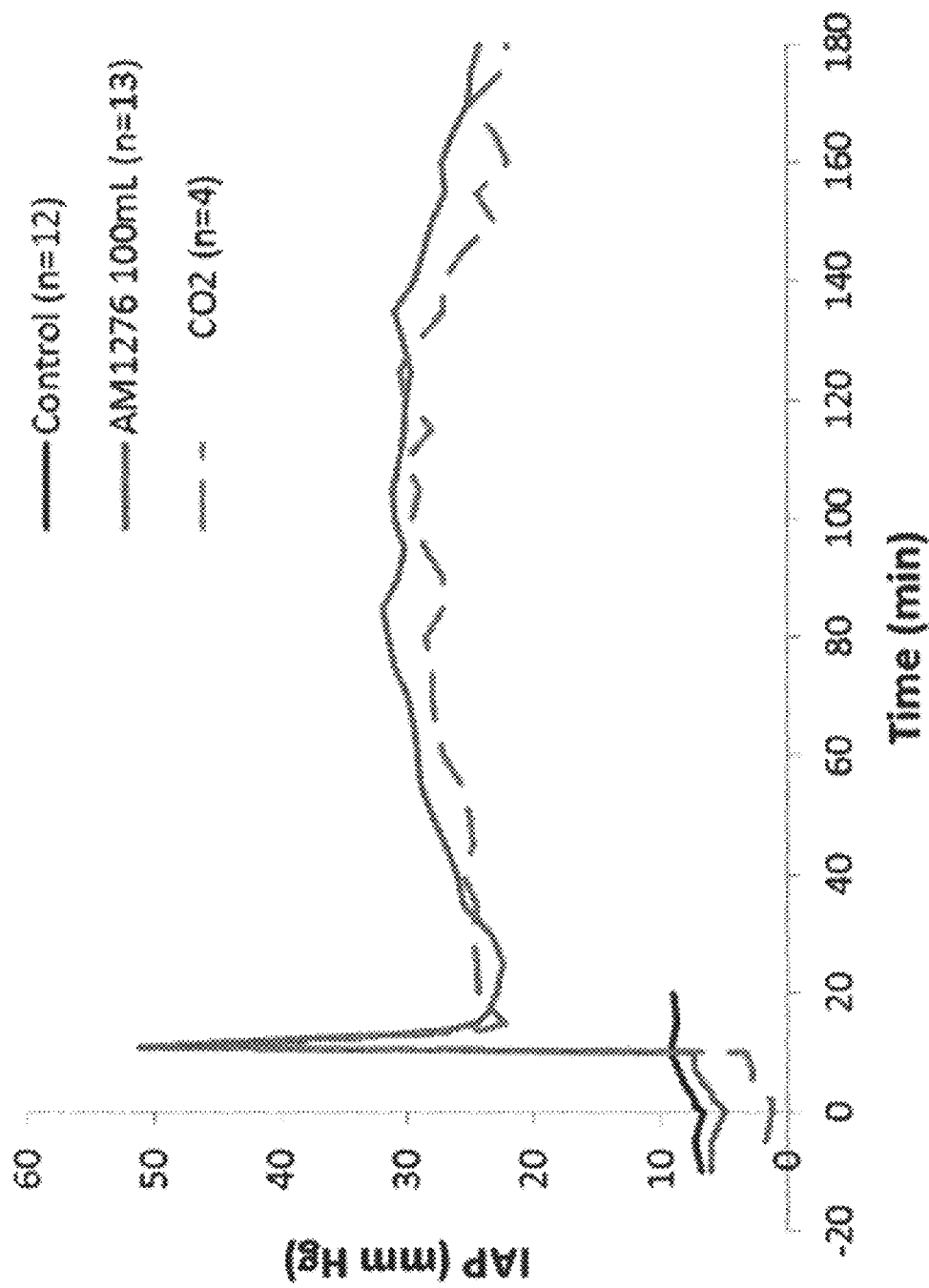

FIG. 7 plots intra-abdominal pressure over time for animals given in situ forming foam, gas insufflation, or no treatment.

Figure 8:
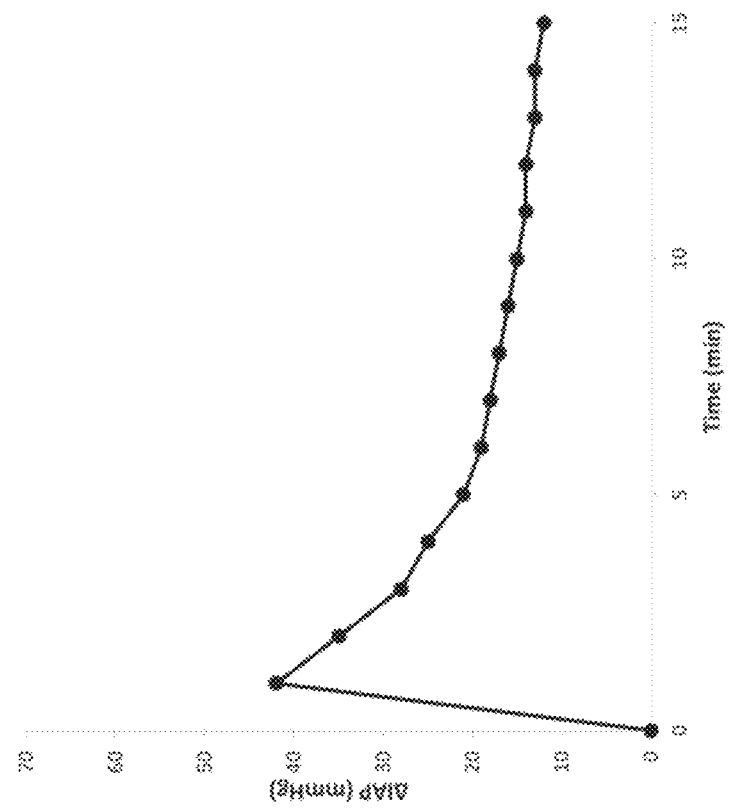

FIG. 8 plots intra-abdominal pressure over time in recently deceased cadaver samples following delivery of an in situ forming foam formulation.

Figure 9:
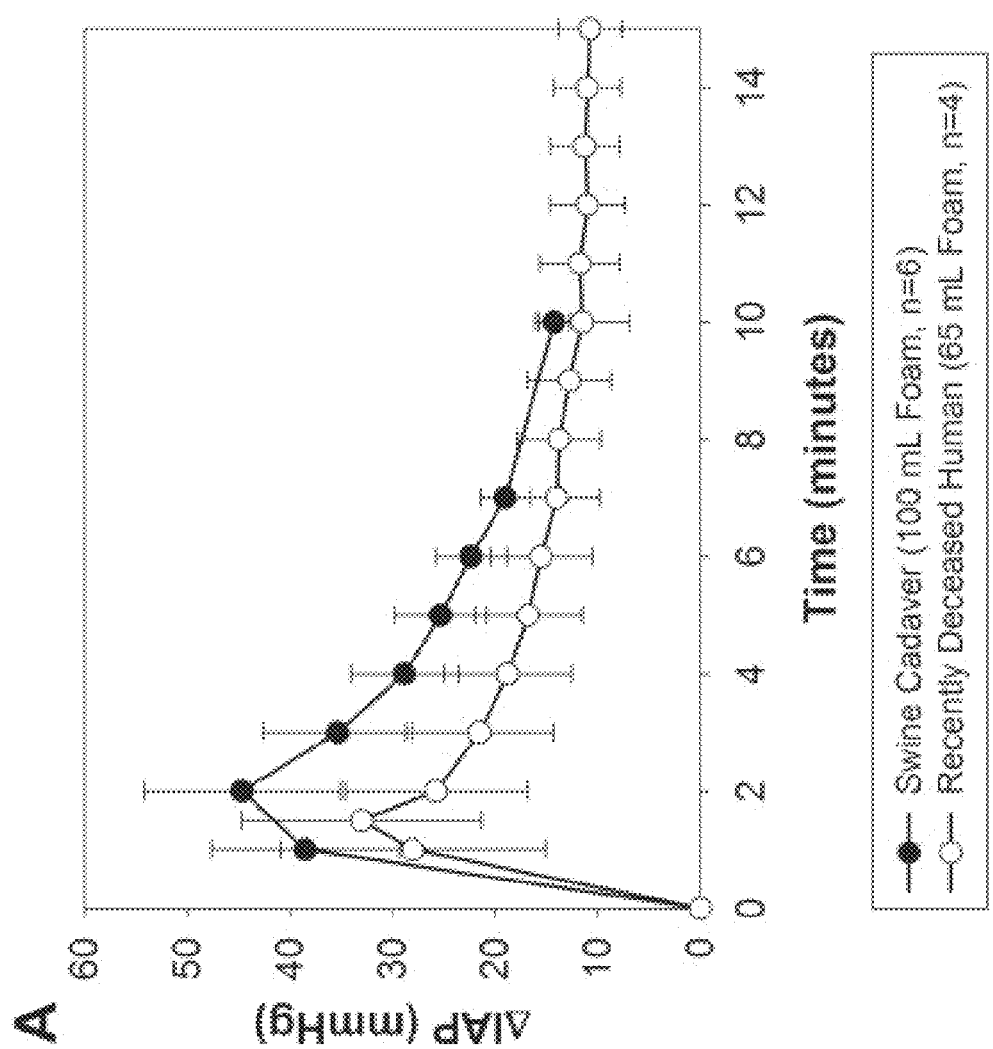

FIG. 9 plots intra-abdominal pressure over time in recently deceased subjects (open circles) and swine (closed circles) following delivery of an in situ forming foam formulation.

Figure 10:
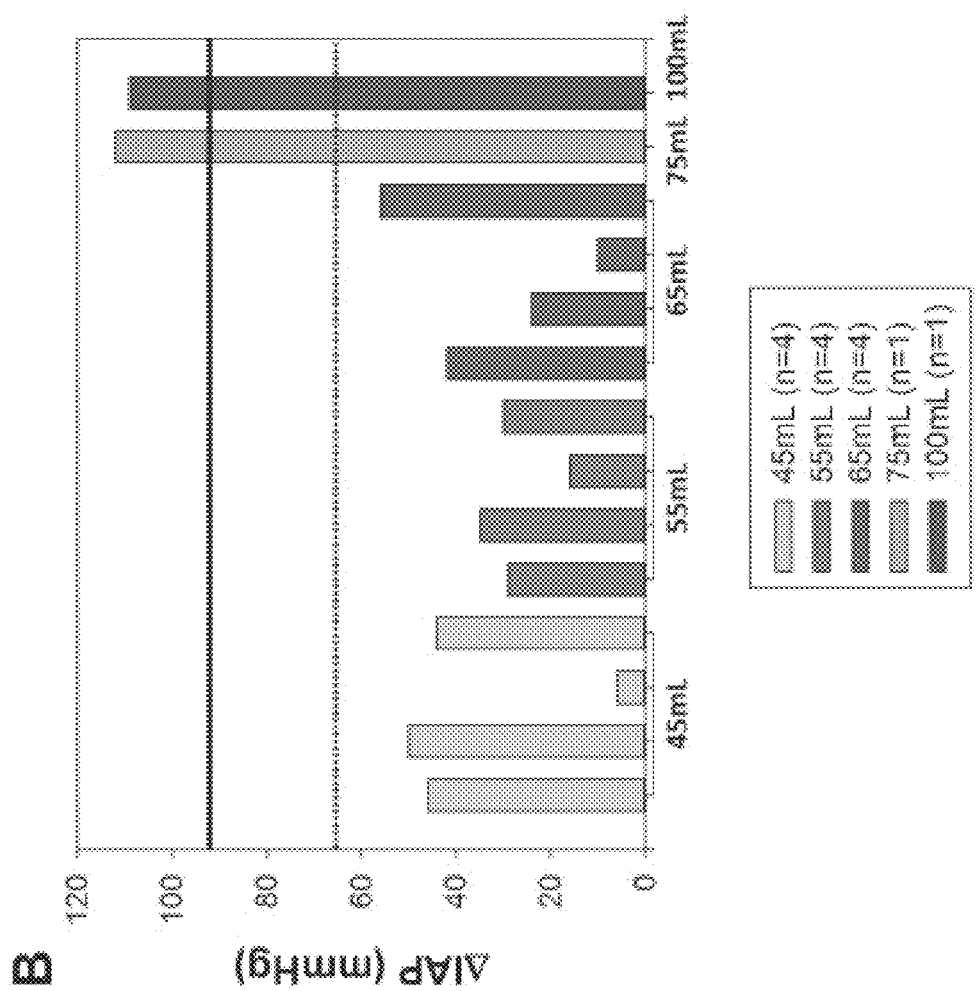

FIG. 10 is a bar graph illustrating peak intra-abdominal pressure observed in recently deceased subjects following delivery of an in situ forming foam formulation at varying doses.

Figure 11:
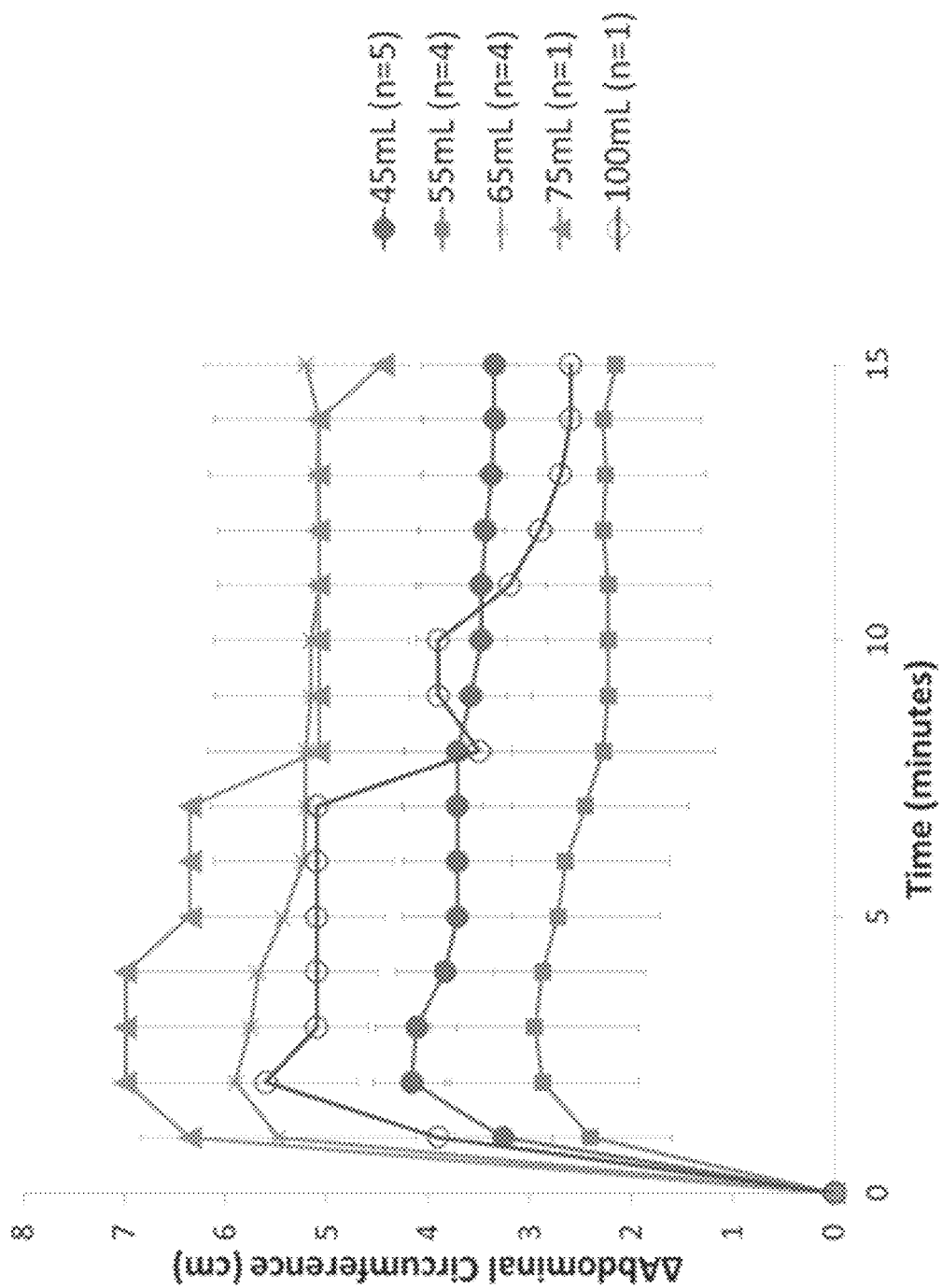

FIG. 11 plots change in circumference at the umbilicus over time in recently deceased subjects following delivery of an in situ forming foam formulation at varying doses.

Figure 12:
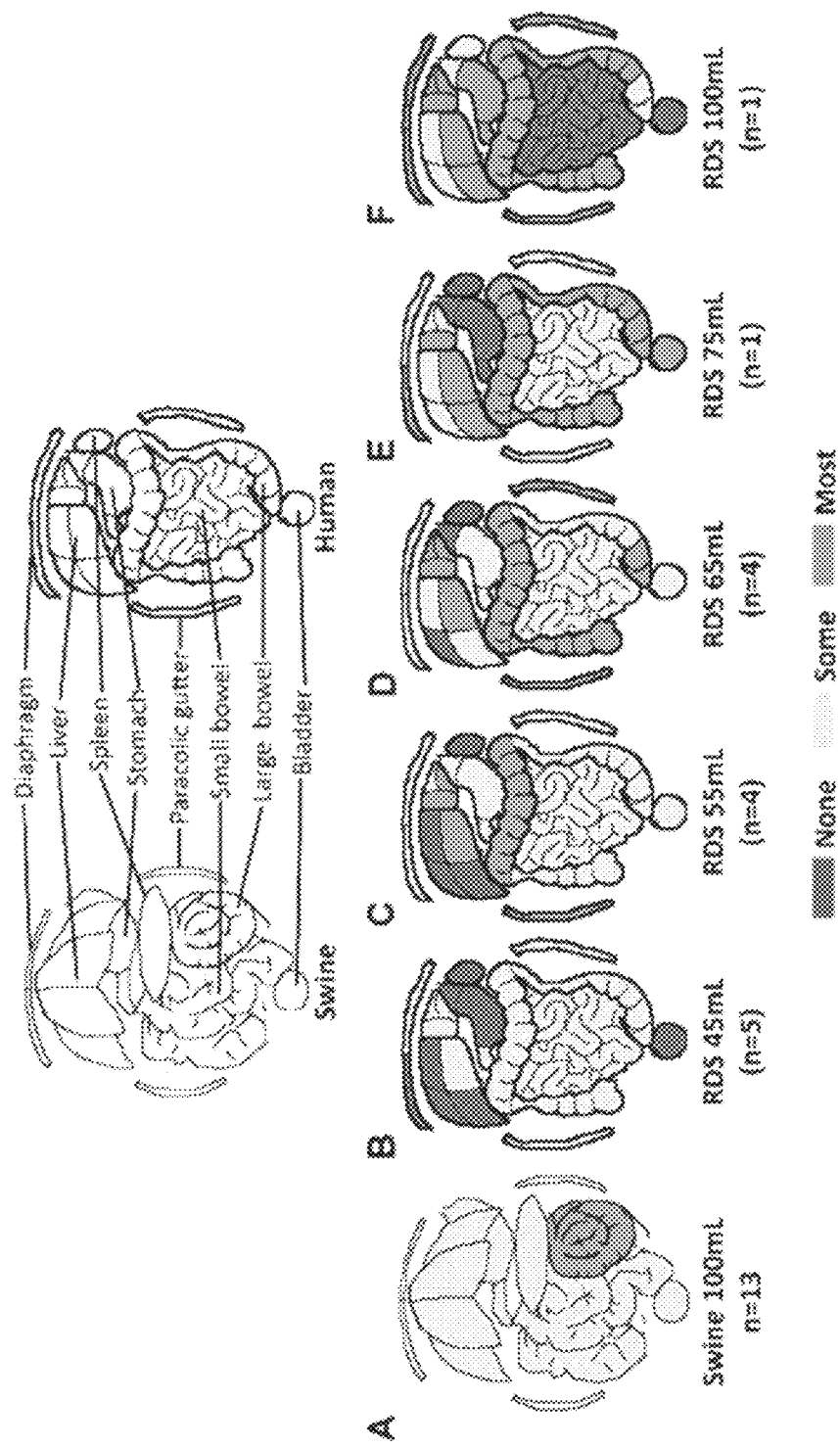

FIG. 12 is a graphical representation of abdominal organ contact in recently deceased subjects following delivery of an in situ forming foam formulation at varying doses. Swine data are shown for reference in A; recently deceased study data are shown in B-F.

Figure 13A:
Figure 13B:
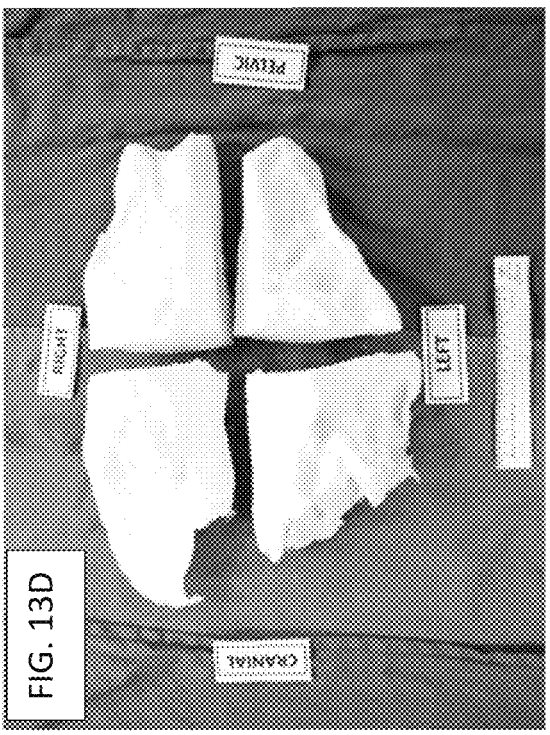
Figure 13C:
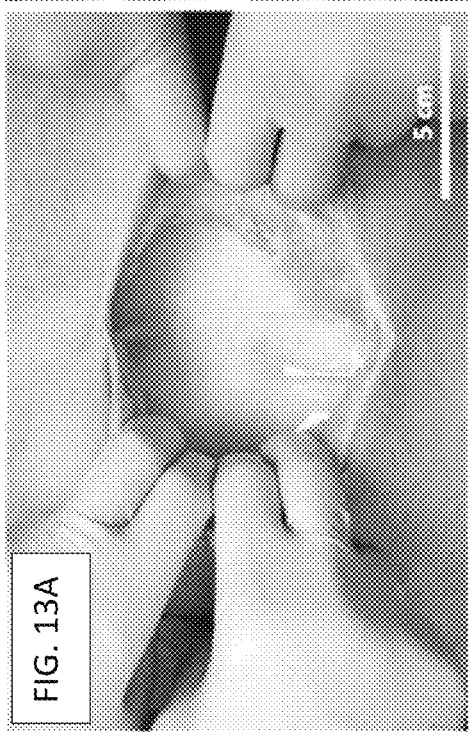
Figure 13D:
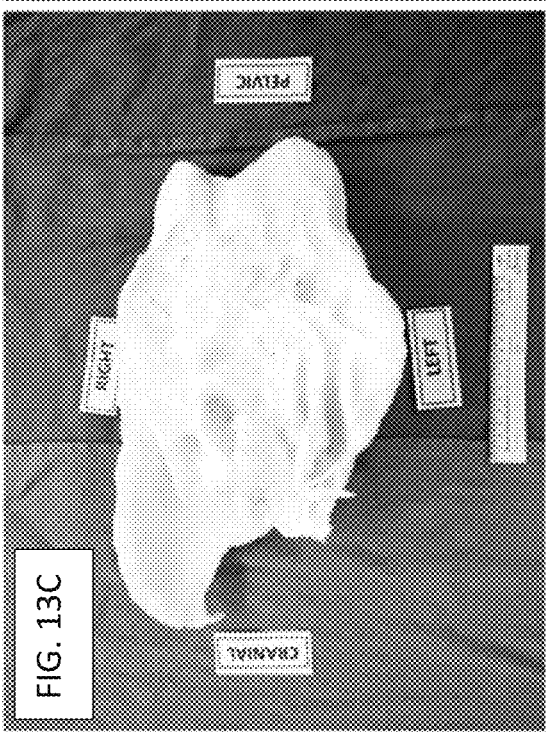

FIG. 13A is a representative photographic image of foam appearance during removal. FIG. 13B is a representative photographic image of foam appearance at a later point during removal. FIG. 13C is a representative photographic image of foam appearance after removal. FIG. 13D is another representative photographic image of foam appearance after removal.

DETAILED DESCRIPTION OF THE PREFERRED EMBODIMENTS

Animal Models

In situ forming polymer foams were deployed at varying dosages in two animal models of hemorrhage: First, a lethal grade V hepatic and portal vein injury in swine, as described in Duggan M J, et al. "Development of a lethal, closed-abdomen grade V hepatoportal injury model in non-coagulopathic swine." J. Surg. Res. 2013 Jun. 1; 182(1): 101, 107 ("Duggan 1"), which is hereby incorporated by reference in its entirety and for all purposes. In this model, wires were placed strategically around the hepatic vasculature and externalized percutaneously. After closure of a midline incision, the wires were pulled, resulting in a severe, uncontrolled, closed-cavity injury and sudden, massive hypotension. In the absence of intervention the injury was over 90% lethal at one hour.

The second model was a lethal arterial injury, in which a wire was placed around the external iliac artery and externalized percutaneously as above as described in Duggan M J, et al. "Development of a lethal, closed-abdomen, arterial hemorrhage model in non-coagulopathic swine." J. Surg. Res. 2014; 187: 536-541 ("Duggan 2"), which is hereby incorporated by reference in its entirety and for all purposes. Also as above, following closure of a midline incision, the wire was pulled, resulting again in a severe, uncontrolled, closed cavity injury, and massive hypotension which was over 80% lethal at one hour in the absence of intervention.

These models were selected to approximate certain conditions in which the systems and methods of the current invention are used, namely intra-cavity and/or noncompressible hemorrhages, or hemorrhages which result in sudden and severe hypotension and/or which are lethal in the absence of an intervention.

In both models, the hemorrhage was generated in, and foams were deployed into, the abdominal cavity. The pressure within the abdomen (the "intra-abdominal pressure" or "IAP") was measured in all animals by continually monitoring bladder pressure through an intraabdominal pressure device (Abviser), consistent with clinical practice in measurement of IAP.

In Situ Forming Foams

According to various embodiments of the invention, a patient suffering from a closed-cavity or non-compressible hemorrhage is treated by administering an in situ forming foam as described in Zugates I and II and Sharma I and II. In preferred embodiments, the liquid phases include (a) an isocyanate to generate gas and crosslink and (b) a polyol to control the foam properties upon reaction with the isocyanate. The formulation reacts to generate a foam within two minutes of its deployment into the body, and is characterized by the parameters shown in Table 1, below.

TABLE 1

PHYSICAL CHARACTERISTICS OF FOAMS USED

| | |
|---|---|
| VOLUME EXPANSION: | 26.2-85.3 fold |
| COMPRESSION FORCE DEFLECTION (CFD) AT 50% DEFLECTION: | 2.2-10.1 kPa |
| WATER UPTAKE: | 2.7-7.7 g/g |
| RISE TIME: | 47.4-80.4 s |

In preferred embodiments, administration of foams of the invention cause a rapid, transient increase or spike in pressure within the cavity or within a portion of a boundary of a cavity containing a hemorrhage. Following the spike the pressure preferably remains elevated at a steady-state value or within a steady-state range that is less than the peak pressure for an extended period of time. Exemplary temporal pressure profiles which include spikes and steady-state pressure ranges are shown for various doses of foam in FIG. 1. The steady-state pressure may persist for a suitable interval which permits evacuation of the patient to a site where medical treatment is available, for instance about 60, 90, 120, 150, 180, 210 or 240 minutes, or longer. The magnitude of the pressure spike may vary depending on the formulation and dose used, so that different device formulations and/or doses might be selected to suit different applications and different patient body sizes or types. Additionally, the magnitude of the steady state pressure may be dose dependent, and may be affected by interventions which affect the rate of foaming, cross-linking, or degradation of the foam. For instance, in some embodiments, a user may decrease a steady-state pressure by applying a material which tends to degrade the foam in a quantity selected to rapidly degrade a portion of the foam. In other embodiments, the delivery system may modulate peak or steady state pressure through a dose modulation feature, a relief valve, or a similar feature. Exemplary materials are described in Sharma I and in Zugates I and II. Delivery systems and methods suitable for use in connection with methods of the present invention are set forth in Sharma II.

The pressure spike ensures that sufficient force is applied to the boundaries of the body cavity and/or the injury site to effectively close hemorrhaging. Studies by others have generally shown that sustained, elevated pressure within body cavities, and particularly elevated IAP above 20 mmHg can have adverse effects on patients. For example, Vivier et al. ("Effects of increased intra-abdominal pressure on central circulation", Br. J. Anaesthesia 96(6): 701-7 (2006), which is hereby incorporated by reference for all purposes), found vascular changes including increases in left ventricular end-diastolic area and pressure (markers of increased cardiac preload) were significantly increased at elevated IAP values.

Sustained IAP values of 20 mmHg and concomitant organ system failure are classified as "compartment syndrome," a condition characterized by pain, paralysis, paresthesia, and other undesirable effects including, in some instances, lethality. In compartment syndrome, increased compartmental pressure limits blood supply to muscles and nerves within the compartment. In an effort to avoid undesirable changes in circulation and/or compartment syndrome, prior art systems and methods have been designed to limit applied compartmental pressures to values below about 20 mmHg or about 30 mmHg.

In spite of the risks associated with sustained, elevated IAP, some studies have suggested that elevated IAP may be useful in reducing hemorrhage in some animal models. For example, Sava, et al., "Abdominal insufflation for prevention of exsanguination," J. Trauma 2003, March; 54(3): 590-4 found that, in a swine model in which a 2.7 mm hole was made in the inferior vena cava in which animals were euthanized after 15 minutes of monitoring, $CO_2$ insufflation resulted in significantly lower blood loss and significantly higher arterial pressure relative to control. Velmahos, et al. "Abdominal insufflation decreases blood loss without worsening the inflammatory response: implications for prehospital control of internal bleeding" found that, in a swine model involving a lacerated spleen, $CO_2$ insufflation reduced blood loss relative to control. Finally, Jaskille, et al. "Abdominal insufflation decreases blood loss and mortality after porcine liver injury." J. Trauma 2005 December; 59(6) 1305-8; discussion 1308, found that $CO_2$ insufflation at 20 cm $H_2O$ in a swine model of blunt liver trauma reduced blood loss by 69%. (Each of the foregoing references is hereby incorporated by reference for all purposes.) However, these studies have not found elevated IAP to be completely effective in reducing hemorrhage or improving survival of lethal abdominal hemorrhages, and they have not demonstrated extended survival without significant adverse effects.

The inventors have found that pressure profiles such as those shown in FIG. 1 are effective in treating life-threatening non-compressible hemorrhage in swine (as discussed in greater detail below), while avoiding complications associated with compartment syndrome. Without wishing to be bound to any theory, it is believed that a transient application of high-pressure within a cavity rapidly prevents ongoing hemorrhage from injured vasculature and permits clots formation in the absence of robust ongoing flow. The application of a lower, but still elevated steady-state pressure maintains hemostasis.

The inventors have also found that, while pressure alone is sufficient to achieve some reduction in hemorrhage, and to improve survivability from non-compressible hemorrhage, the application of pressure by a foam such as an in situ forming foam or another material having a solid or partially solid surface improves the efficacy of the systems and methods of the invention. While pressures may be applied by a variety of means, including gas or liquid insufflation, the use of foams to treat hemorrhages in cavities may be particularly advantageous. Though not wishing to be bound to any theory, it is believed that three characteristics of the foams described above and in Sharma I and Zugates I and II are particularly useful in treating hemorrhages: first, the in situ reaction of the foam device spontaneously creates a transient increase in pressure, followed by a return to steady state. The foam system does not require monitoring or feedback systems. Second, the foam system is portable and easily administered. Third, the material provides a solid, steady source of intraabdominal pressure. It does not readily leak, nor is it generally absorbed by the body. Therefore, the pressure does not need to be maintained by the addition of materials.

In spite of the advantages of in situ forming foams for treatment of hemorrhages in cavities, other treatment systems and methods are within the scope of the invention insofar as it is possible to achieve the pressure profiles discussed above using these systems and methods. As non-limiting examples, gels, elastomeric solids, pre-formed foams, or combinations of foams and liquids or foams and gasses can be utilized to apply pressure to the cavity or a portion of the boundary of the cavity (including injured tissue and tissues adjacent to injured tissue). Additionally, materials which undergo phase changes within cavities, for example reverse thermosensitive materials including poloxamers, and electromechanical or hydraulic devices can be used to deliver pressure to hemorrhages within cavities. And pressure may be delivered via materials, systems and devices deployed either within the cavity or outside of the cavity (e.g. adjacent to the cavity). In some embodiments, the cavity is constricted from the outside, for example by constricting the abdomen from the exterior.

Pressure can be generated in certain models through the delivery and/or removal of material (e.g. liquid, gas, gel, foam) to apply pressure to the cavity, and the pressure applied may be controlled manually by an end user, mechanically by a governing device such as a valve (e.g. a check valve), or by computerized means.

The principles of the invention in its various embodiments are further illustrated by the following non-limiting examples:

Example 1: Dose-Dependent Changes in Spike and Steady-State Pressure Values and Survival in a Hepatic Hemorrhage Model In situ forming foams were delivered in the grade V hepatic-portal model described above. Animals were given 64 ml, 85 ml, 100 ml or 120 ml of liquid-phase in situ forming foam formulations, or sham treatment in the case of control animals, and IAP was measured over an interval of 3 hours. As shown in FIG. 1, control animals showed only a minor increase in IAP over the first 20 minutes of the experiment, while foam-treated animals displayed dose-dependent changes in spike pressures and steady-state pressures. In addition, survival was quantitated for animals in each treatment category.

Foam dosages in the swine models used herein are likely to be larger than the volumes used in humans, owing to differences in the volume of the abdominal cavity.

The control group was lethal in 11 of 12 animals (8.3% survival), with a median survival time of 23 minutes (quartile 20-38). Survival rate with hepato-portal injury was highest at the 120 ml dose (90%; p=0.0002) and decreased in a dose-dependent fashion: 100 ml (72.2%; p=0.0007), 85 ml (33.3%; p=0.22), and 64 ml (16.7%; p=0.47). The Kaplan-Meier graph of all groups is shown in FIG. 2. Median survival time was 180 (180-180) minutes at 120 mL, 180 (161-180) minutes at 100 mL, 89 (81-158) minutes at 85 mL, and 55 (40-68) at 64 mL. Relative to controls, survival time as measured by the log-rank test was significantly improved in all groups. Hemorrhage rate was also reduced in all groups, but lowest in the 120 mL dose group vs. control group (0.34±0.052 vs. 3.0±1.3 ml/kg/min, p=0.001).

A relationship was also identified between peak (spike) pressure and survival time in swine. FIG. 3 plots survival time against peak pressure values observed in 69 pooled experiments. A significant survival benefit was observed for higher peak pressures as described in the Table 2:

TABLE 2

MEAN SURVIVAL TIME AS A FUNCTION OF PEAK IAP.

| Peak IAP (mmHg) | Mean survival time (min) |
|---|---|
| <20 | 46 |
| 20 to 69 | 141 |
| >69 | 170 |

A relationship was also identified between steady-state pressure and survival time in swine. FIG. 4 plots the IAP measured 30 minutes after injury against survival time, and indicates that survival improved at steady-state pressures at or above 18 mmHg, and improved further at steady state pressures at or above 28 mmHg (see Table 3):

TABLE 3

MEAN SURVIVAL TIME AS A FUNCTION OF IAP AT 30 MINUTES POST-INJURY.

| IAP at 30 minutes post-injury (mmHg) | Mean survival time (min) |
|---|---|
| >28 | 55 |
| 14 to 28 | 149 |
| >28 | 165 |

Example 2: Dose-Dependent Changes in Spike and Steady-State Pressure Values and Survival in an Arterial Hemorrhage Model Similar experiments were conducted in the arterial hemorrhage model described above. As shown in FIGS. 5 and 6, dose dependent effects on IAP and survival were observed in this model as well. There was a noticeable increase in percent survival at 1 hour for the 120 ml and 100 ml test groups relative to the control group (84% and 82%, respectively, vs. 14%; p<0.001). Hemorrhage rate at the experimental endpoint was significantly lower in both foam groups relative to the control.

By way of summary of the foregoing examples, Table 4 below depicts six exemplary experiments in which varying quantities of an in situ foaming formulation was administered to porcine in a liver hemorrhage and an iliac hemorrhage model.

TABLE 4

TRANSIENT PEAK AND STEADY STATE PRESSURES OBSERVED IN VARIOUS EXPERIMENTS.

| | Liver Hemorrhage Model | | Iliac Artery Hemorrhage Model | |
|---|---|---|---|---|
| Swine Foam Dose | Peak Pressure (mmHg) | Steady State Pressure (mmHg) | Peak Pressure (mmHg) | Steady State Pressure (mmHg) |
| 120 mL | 86 | 28 | 44 | 16 |
| 100 mL | 51 | 25 | 22 | 12 |
| 85 mL | 21 | 18 | — | — |
| 64 mL | 14 | 14 | — | — |

All doses tested here demonstrated safety and a survival benefit. As the table illustrates, the peak pressures observed range from 14 to 86 mmHg in the liver hemorrhage model and from 22 to 44 mmHg in the iliac artery across both hemorrhage models. Steady state values ranged from 12 to 20 mmHg in both injury models.

Example 3: Approximation of Survival Effects by Gas Insufflation with Foam-Like Pressure Kinetics While not wishing to be bound to any theory, it is believed that the foams disclosed above and used in the previous examples generated pressure spikes by one or more of a rapid increase in the volume of the foam, gas generated from the blowing reaction, gas generated and not fully contained by the foam, etc. The reduction in pressure to the steady state values, in turn, may have been due to one or more of a viscoelastic response of the tissues in the abdominal cavity, a change in fundamental abdominal volume, possibly caused by the relaxation of tissues in the abdomen, a reduction in the volume of the foam, gas transfer, etc.

In the models examined, larger doses of foam were associated with larger peak pressures, as shown in FIG. 1, and with improved survival, as shown in FIG. 2. To examine the relationship between the survival effect and the IAP profiles achieved, controls and animals treated with 100 ml of foam formulation were compared with animals treated by a $CO_2$ gas insufflation protocol which approximated the pressure profile observed in foam treated animals. The various IAP measurements from the three groups are presented in FIG. 7. In gas treated animals, 1-hour survival was about 75%, while three hour survival was about 50%. Although these values did not match those seen in the highest-dose cohorts of foam-treated animals, they did suggest that employing gas insufflation or another pressure-generating technique to achieve a pressure profile that includes a transient spike or peak followed by a steady state pressure is a potentially effective treatment for hemorrhage.

Example 4: Observation of Spike-and-Steady State Pressure Profiles in Recently Deceased Human Subjects To understand performance in representative human anatomy, the Arsenal Foam System was deployed in recently deceased human subjects. Subjects with no abdominal pathology or prior surgery were identified and informed consent was obtained from family members post-mortem. Within three hours of death, the abdomen was accessed and 1500 mL fluid was added to simulate severe hemorrhage. Self-expanding polyurethane foam was administered at multiple doses using a prototype delivery system. Intraabdominal pressure was monitored as a function of time for 15 minutes, after which the foam was removed and contact with abdominal tissues was evaluated.

The Arsenal Foam System was successfully deployment in 10 subjects within three hours post-mortem. Intraabdominal pressure was recorded, as shown for a representative sample in FIG. 8

Foam administration resulted in a rapid, transient, and dose-dependent peak in intraabdominal pressure following deployment in humans. Notably, the shape of the curves was similar to that observed in animal models, suggesting that the foam system results in a characteristic intraabdominal pressure following deployment.

Because subjects in this study were not alive, safety and efficacy of the foam at varying doses could not be measured directly. However, pressure can be used as a surrogate endpoint to link results in swine to results in recently deceased humans. These results suggest that the intraabdominal pressure profiles observed in swine can be matched in humans. While not wishing to be bound by any theory, it is believed that human doses which result in the intraabdominal pressure profiles observed to be effective in swine models will be safe and effective in humans.

Example 5: Dose-Ranging Foam Performance in Recently Deceased Human Subjects

The study described in Example 4 was conducted across a range of foam doses with initial volumes. Terminal patients were identified, and the study was conducted within three hours of death. The abdomen was accessed and 1500 mL fluid was added to simulate abdominal hemorrhage. Self-expanding foam was delivered at multiple doses (initial volumes of 45, 55, 65, 75, and 100 mL). Intra-abdominal pressure was monitored for 15 minutes, then foam was removed via laparotomy to assess abdominal tissue contact.

N=21 recently deceased patients ranging in age from 20 to 92 years and BMI 18 to 39 kg/m$^2$ were enrolled in the study. Administration of foam at doses ranging from 45 to 100 mL resulted in final foam volumes ranging between 911 and 3165 mL. This corresponds to foam volume expansion ranging between 21-fold and 43-fold the initial volume. Material properties of the foam in these studies are reported in Table 5:

TABLE 5

MATERIAL PROPERTIES OF SELF-EXPANDING FOAM IN RECENTLY DECEASED HUMAN SUBJECTS

| Parameter | Observed Range |
|---|---|
| Expansion | 21x-43x |
| Final Volume | 911-3165 mL |
| Compression Force Deflection | 4.9-9.2 kPa |
| Water Uptake | 3.7-9.5 g/g |

Foam administration resulted in a characteristic intra-abdominal pressure curve wherein pressure increased rapidly to reach a peak pressure, then dissipated toward baseline levels. The intra-abdominal pressure profile was similar in recently deceased human subjects and in swine, as indicated in FIG. 9.

As seen from FIG. 10, 45 mL, 55 mL, and 65 mL doses in recently deceased human subjects resulted in peak pressures of 37±20, 28±8.1, and 33±20 mmHg, respectively, within the acceptable range established in swine studies, shown as horizontal lines in FIG. 10. On the other hand, 75 mL and 100 mL foam deployments exceeded acceptable pressures defined in swine.

In this study intra-abdominal pressure in recently deceased human subjects increased to peak levels between 13 and 125 mmHg (absolute levels). Adjusting for variations in subject baseline pressure, peak abdominal pressure varied between 6 and 112 mmHg (FIG. 10).

Foam treatment resulted in distension of the abdominal cavity in recently deceased human subjects. In this regard, the circumference at the umbilicus was measured and was found to increase between 0.6 and 9.5 cm within two minutes of foam deployment as shown in FIG. 11. Distension was not observed to be dose dependent.

Foam conformed to human anatomy and contacted organs throughout the abdomen. Organ contact was dose dependent as illustrated in the graphical representation of abdominal organ contact shown in FIG. 12. Foam was found to contact the following organs: bladder, small bowel, large bowel, omentum, liver, spleen, paracolic gutters, and the diaphragm. More widespread distribution throughout the abdomen was generally observed with increasing initial foam doses. Swine data are shown in A; recently deceased study data are shown in B-F. Contact with the omentum is not depicted, as the omentum frequently overlapped the small bowel and prevented organ contact.

Foam was removed from the abdomen. Representative images of foam appearance during and after removal are shown in FIGS. 13A-D. After removal from the abdomen, foam was measured along the midline to determine the distance between the cranial and pelvic edges of the foam, the left and right edges, and the depth measured from the bottom of the foam to the top of the foam. The dimensions of foams administered in this study are shown in Table 6:

TABLE 6

MATERIAL PROPERTIES OF SELF-EXPANDING FOAM IN RECENTLY DECEASED HUMAN SUBJECTS.

| Dimension | Observed Range |
|---|---|
| Cranial-Caudal Distance | 19-40 cm |
| Left-Right Distance | 18-36 cm |
| Depth | 6.5-15 cm |

Without being bound to theory, it is believed that human doses which result in the intra-abdominal pressure profiles observed to be effective and safe in swine models will be safe and effective in humans.

CONCLUSION

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a nonlimiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "cavity" as used herein means closed body compartments such as the abdominal cavity, the thoracic cavity, etc., as well as cavities that are open, such as junctional wounds, and "pseudocavities" in which at least one boundary of the cavity is defined by a structure other than an organ or a tissue, (e.g. a bandage).

The term "consists essentially of" means excluding other materials that contribute to function, unless otherwise defined herein. Nonetheless, such other materials may be present, collectively or individually, in trace amounts.

As used in this specification, the term "substantially," "approximately" or "about" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of treating a hemorrhage within a cavity of a patient, comprising the steps of:
    applying a pressure to an interior boundary of the cavity, wherein the pressure is applied by an article placed into the cavity and is characterized by a transient peak value, and wherein the article is a material, which is formed inside of the cavity by applying a formulation comprising at least one liquid phase into the cavity.

2. The method of claim 1, wherein the transient peak value less than about 84 mmHg.

3. The method of claim 1, wherein the transient peak value is at least about 51 mmHg.

4. The method of claim 1, wherein the transient peak value is at least about 20 mmHg.

5. The method of claim 1, wherein the pressure is characterized by at least one steady state value.

6. The method of claim 1, wherein the cavity is a human abdominal cavity.

7. The method of claim 1, wherein the formulation is applied in a dosage ranging from 45 mL to 100 mL.

8. The method of claim 1, wherein the formulation is applied in a dosage ranging from 45 mL to <75 mL.

9. The method of claim 1, wherein the formulation is applied in a dosage ranging from 45 mL to 65 mL.

10. The method of claim 1, wherein a volume of the material that is formed ranges from 900 mL to 3200 mL.

11. The method of claim 1, wherein the material is a foam.

12. The method of claim 11, wherein the at least one liquid phase includes (a) an isocyanate phase to generate gas and crosslink and (b) a polyol phase to control foam properties upon reaction with the isocyanate.

13. The method of claim 11, wherein the formulation reacts to generate a foam within two minutes of its deployment into the cavity of the patient.

* * * * *

UNITED STATES PATENT AND TRADEMARK OFFICE
CERTIFICATE OF CORRECTION

PATENT NO. : 9,820,749 B2
APPLICATION NO. : 14/597993
DATED : November 21, 2017
INVENTOR(S) : Adam Rago et al.

Page 1 of 1

It is certified that error appears in the above-identified patent and that said Letters Patent is hereby corrected as shown below:

In the Specification

Column 1, Line 1 - insert:
--STATEMENT REGARDING FEDERALLY SPONSORED RESEARCH
This invention was made with Government support under contract no. W911NF-10-C-0089 awarded by the Defense Advanced Research Projects Agency (DARPA). The Government has certain rights in the invention.--

Signed and Sealed this
Tenth Day of July, 2018

Andrei Iancu
*Director of the United States Patent and Trademark Office*